United States Patent
Rögl

(10) Patent No.: US 11,724,978 B2
(45) Date of Patent: Aug. 15, 2023

(54) METHOD FOR OXIDIZING A 1,1,-BIS-(3,4-DIMETHYLPHENYL)-ALKANE TO 3,3',4,4'-BENZOPHENONE TETRACARBOXYLIC ACID

(71) Applicant: Evonik Fibres GmbH, Schörfling am Attersee (AT)

(72) Inventor: Harald Rögl, Wallern an der Trattnach (AT)

(73) Assignee: EVONIK FIBRES GMBH, Schörfling am Attersee (AT)

( * ) Notice: Subject to any disclaimer, the term of this patent is extended or adjusted under 35 U.S.C. 154(b) by 339 days.

(21) Appl. No.: 17/123,004

(22) Filed: Dec. 15, 2020

(65) Prior Publication Data
US 2021/0179527 A1    Jun. 17, 2021

(30) Foreign Application Priority Data
Dec. 16, 2019   (EP) ..................................... 19216393

(51) Int. Cl.
| | | |
|---|---|---|
| C07C 51/275 | (2006.01) | |
| C07C 51/43 | (2006.01) | |
| C07C 65/34 | (2006.01) | |
| B01J 3/02 | (2006.01) | |
| B01J 19/00 | (2006.01) | |
| C01B 21/40 | (2006.01) | |

(52) U.S. Cl.
CPC ............... *C07C 51/275* (2013.01); *B01J 3/02* (2013.01); *B01J 19/0013* (2013.01); *C01B 21/40* (2013.01); *C07C 51/43* (2013.01); *B01J 2219/00029* (2013.01); *B01J 2219/00051* (2013.01); *C07C 65/34* (2013.01)

(58) Field of Classification Search
CPC ........ C07C 51/275; C07C 65/34; C07C 51/43
USPC ........................................................ 562/410
See application file for complete search history.

(56) References Cited

U.S. PATENT DOCUMENTS

| | | |
|---|---|---|
| 3,078,279 A | 2/1963 | McCracken et al. |
| 3,466,301 A | 9/1969 | McCracken et al. |
| 3,479,400 A | 11/1969 | Lese et al. |
| 3,671,579 A | 6/1972 | Joyce et al. |
| 4,173,573 A | 11/1979 | Onopchenko et al. |
| 4,684,738 A | 8/1987 | Fujiwara et al. |
| 7,687,668 B2 | 3/2010 | Rögl et al. |
| 7,812,099 B2 | 11/2010 | Rögl et al. |
| 9,469,048 B2 | 10/2016 | Ungerank et al. |
| 10,040,036 B2 | 8/2018 | Ungerank et al. |

FOREIGN PATENT DOCUMENTS

| | | |
|---|---|---|
| JP | S61103851 | 5/1986 |
| JP | S62198644 | 9/1987 |

OTHER PUBLICATIONS

Extended European Search Report for corresponding European application 19 21 6393 dated Jun. 8, 2020.
Schulz, et al., "Nitric Acid Oxidation of Dixylyehtane to Benzophenone Tetracarboxylic Acid," *Ind. Eng. Chem. Prod. Res. Dev.* 15(2):152-156 (Jun. 1976).
English language machine translation of JPS61103851 submitted with an abstract only in an IDS on Jan. 10, 2021.
English language machine translation of JPS62198644 submitted with an abstract only in an IDS on Jan. 10, 2021.

*Primary Examiner* — Ana Z Muresan
(74) *Attorney, Agent, or Firm* — Law Office of: Michael A. Sanzo, LLC

(57) ABSTRACT

In a method for oxidizing 1,1-bis-(3,4-dimethylphenyl)-alkane with nitric acid in a pressure vessel to produce 3,3',4,4'-benzophenone tetracarboxylic acid with concurrent formation of nitric oxide, passing nitric oxide from the pressure vessel into an absorption vessel and reacting nitric oxide in the absorption vessel with molecular oxygen and water to produce an aqueous nitric acid solution prevents discharge of nitric oxide, avoids the risk of oxygen inhibiting the nitric acid oxidation and reduces nitric acid consumption when the nitric acid from the absorption vessel is used for oxidizing the 1,1-bis-(3,4-dimethylphenyl)-alkane.

20 Claims, No Drawings

METHOD FOR OXIDIZING A 1,1,-BIS-(3,4-DIMETHYLPHENYL)-ALKANE TO 3,3',4,4'-BENZOPHENONE TETRACARBOXYLIC ACID

CROSS REFERENCE TO RELATED APPLICATIONS

The present application claims priority under 35 USC § 119 to application EP 19216393.9, filed in Europe on Dec. 16, 2019, the contents of which is incorporated herein by reference in its entirety.

FIELD OF THE INVENTION

The invention is directed at a method for oxidizing a 1,1-bis-(3,4-dimethylphenyl)-alkane to 3,3',4,4'-benzophenone tetracarboxylic acid which can be used for producing 3,3',4,4' benzophenone tetracarboxylic acid dianhydride

BACKGROUND OF THE INVENTION 3,3',4,4'-benzophenone tetracarboxylic acid dianhydride is useful as a monomer for preparing aromatic polyimides. Polyimides made from this monomer have been commercialized under the trade name P84.

U.S. Pat. No. 3,078,279 discloses preparation of 3,3',4, 4'-benzophenone tetracarboxylic acid dianhydride by oxidizing 1,1-bis-(3,4-dimethylphenyl)-ethane with 30% by weight nitric acid at 200 to 210° C. The reaction proceeds through intermediates 3,3',4,4'-tetramethylbenzophenone and 3,3',4,4'-benzophenone tetracarboxylic acid as described in J. G. D. Schulz and A. Onopchenko, Ind. Eng. Chem., Prod. Res. Dev. 15 (1976) 152-156. U.S. Pat. No. 3,479,400 discloses a two step oxidation of 1,1-bis-(3,4-dimethylphenyl)-ethane where only a small excess of nitric acid is used in a first oxidation step carried out at 105 to 160° C., a larger excess of more concentrated nitric acid is used in a second oxidation step carried out at about 175° C., and aqueous filtrate obtained by filtering 3,3',4,4'-benzophenone tetracarboxylic acid from the reaction mixture obtained in the second oxidation step is reused to provide the nitric acid for the first oxidation step. These methods have the disadvantage that large amounts of nitric oxide are formed during oxidation of 1,1-bis-(3,4-dimethylphenyl)-ethane to 3,3',4, 4'-benzophenone tetracarboxylic acid and are discharged from the reactor where the oxidation is carried out. The commercial production of 3,3',4,4'-benzophenone tetracarboxylic acid dianhydride by this route therefore requires a costly off-gas treatment.

U.S. Pat. No. 4,173,573 discloses preparation of 3,3',4, 4'-benzophenone tetracarboxylic acid dianhydride by oxidizing 1,1-bis-(3,4-dimethylphenyl)-ethane with 54% by weight nitric acid in a one-step fed batch oxidation where the reaction temperature is raised from 140° C. to 175° C. during the dosing of nitric acid. U.S. Pat. No. 3,466,301 discloses a similar fed batch oxidation with 70% by weight nitric acid where the reaction temperature is raised from 140 ° C. to 170° C. during the dosing of nitric acid.

JPS61-103851 discloses a two-stage oxidation of 1,1-bis-(3,4-dimethylphenyl)-ethane where oxidation with 30% by weight nitric acid is carried out at 180° C. in a closed autoclave for 3 h followed by introducing oxygen gas into the autoclave and continuing the reaction at the same temperature. The gas present in the autoclave at the end of the reaction contains only small amounts of nitric oxide. Comparative example 2 of this document demonstrates that introducing oxygen from the beginning of the nitric acid oxidations strongly inhibits the oxidation reaction. JPS62-198644 and US 4,684,738 disclose nitric acid oxidation of 1,1-bis-(3,4-dimethylphenyl)-ethane at reaction conditions similar to JPS61-103851, continuously introducing oxygen gas into the autoclave and maintaining a pressure of 20 bar by discharging gas. The discharged gas has a low content of nitric oxide. However, these documents do not describe how inhibition of the nitric acid oxidation by oxygen is prevented. Applicant has observed the same inhibiting effect of oxygen as described in JPS61-103851 and has found that introducing oxygen into the pressure reactor during nitric acid oxidation of 1,1-bis-(3,4-dimethylphenyl)-methane led to complete inhibition of the nitric acid oxidation.

Therefore, there is still a need for a process for producing 3,3',4,4'-benzophenone tetracarboxylic acid by nitric acid oxidation of a 1,1-bis-(3,4-dimethylphenyl)-alkane, in particular 1,1-bis-(3,4-dimethylphenyl)-methane, which reduces or prevents discharge of nitric oxide and avoids the risk of oxygen inhibiting the nitric acid oxidation.

SUMMARY OF THE INVENTION

The inventors of the present invention have now found that such a process can be achieved by passing nitric oxide from the pressure vessel, in which nitric acid oxidation of a 1,1-bis-(3,4-dimethylphenyl)-alkane is carried out, into a separate absorption vessel and reacting the nitric oxide in the absorption vessel with molecular oxygen and water to provide an aqueous nitric acid solution.

Subject of the invention is therefore a method for oxidizing a 1,1-bis-(3,4-dimethylphenyl)-alkane to 3,3',4,4'-benzophenone tetracarboxylic acid, comprising a step of reacting the 1,1-bis-(3,4-dimethylphenyl)-alkane or a partial oxidation product thereof with nitric acid in a pressure vessel at a temperature of from 120 to 220° C., providing 3,3',4,4'-benzophenone tetracarboxylic acid with formation of nitric oxide; passing nitric oxide from the pressure vessel into an absorption vessel; and reacting the nitric oxide in the absorption vessel with molecular oxygen and water to produce an aqueous nitric acid solution.

The method preferably comprises the steps:
a) reacting the 1,1-bis-(3,4-dimethylphenyl)-alkane with a first aqueous nitric acid composition at a temperature of from 90 to 115 ° C. to provide a reaction mixture with two liquid phases, an aqueous phase and an organic phase comprising 3,3',4,4'-tetramethylbenzophenone,
b) separating the aqueous phase and the organic phase of step a), and
c) reacting the organic phase separated in step b) with a second aqueous nitric acid composition in the pressure vessel at a temperature of from 120 to 220° C.
In a preferred embodiment, the reaction mixture of step c) is cooled to crystallize 3,3',4,4'-benzophenone tetracarboxylic acid and residual liquid separated from crystallized 3,3',4, 4'-benzophenone tetracarboxylic acid is passed to step a) to provide all or a part of the first aqueous nitric acid composition used in step a).

DETAILED DESCRIPTION OF THE INVENTION

The method of the invention comprises a step of reacting a 1,1-bis-(3,4-dimethylphenyl)-alkane or a partial oxidation product thereof with nitric acid. The partial oxidation product is preferably the corresponding 1,1-bis-(3,4-dimethylphenyl)-alkanol or 3,3',4,4'-tetramethylbenzophenone and most preferably 3,3',4,4'-tetramethylbenzophenone. The method of the invention may also be carried out with a mixture comprising both the 1,1-bis-(3,4-dimethylphenyl)-alkane and 3,3',4,4'-tetramethylbenzophenone. The alkane moiety in the 1,1-bis-(3,4-dimethylphenyl)-alkane is preferably methane, ethane or propane and most preferably methane, i.e. the most preferred 1,1-bis-(3,4-dimethylphenyl)-alkane is 1,1-bis-(3,4-dimethylphenyl)-methane. Suitable 1,1-bis-(3,4-dimethylphenyl)-alkanes and methods for preparing them from ortho-xylene and an aldehyde, such as formaldehyde, acetaldehyde or propionaldehyde are known from the prior art. Preferably, a 1,1-bis-(3,4-dimethylphenyl)-alkane with a high degree of isomer purity with regard to the position of methyl groups in the dimethylphenyl moiety is used. Methods for increasing isomer purity by isomerization reactions or purification methods, such as fractional crystallization, are known from the prior art.

The 1,1-bis-(3,4-dimethylphenyl)-alkane or the partial oxidation product thereof is reacted with nitric acid in a pressure vessel at a temperature of from 120 to 220° C. The reaction is preferably carried out at a pressure higher than the vapor pressure of water at the reaction temperature in order to maintain a liquid reaction mixture. The reaction is most preferably carried out with autogenous pressure, i.e. pressure resulting from vapor generated from water or aqueous nitric acid that has been charged to the pressure vessel before the pressure vessel is heated to the reaction temperature. The reaction is carried out for a time period sufficient to oxidize at least part of the starting material to 3,3',4,4'-benzophenone tetracarboxylic acid. The reaction time is preferably chosen to oxidize at least 50% of the starting material, preferably at least 80% of the starting material and more preferably more than 95% of the starting material to products where methyl groups of the 3,4-dimethylphenyl moieties are oxidized to carboxylic acid groups. Preferably, no oxygen is introduced into the pressure vessel during the reaction of the 1,1-bis-(3,4-dimethylphenyl)-alkane or its partial oxidation product with nitric acid in order to prevent inhibition of the nitric acid reaction by oxygen. In a preferred embodiment, the pressure vessel is flushed with an inert gas, preferably nitrogen, to remove oxygen gas from its interior before it is heated to the reaction temperature.

Oxidation of a 1,1-bis-(3,4-dimethylphenyl)-alkane with nitric acid produces large amounts of nitric oxide as a byproduct. The stoichiometry for oxidizing 1,1-bis-(3,4-dimethylphenyl)-ethane (dixylylethane, DXE) to 3,3',4,4'-benzophenone tetracarboxylic acid (BTA) is

3DXE+34HNO$_3$→3BTA+3CO$_2$+34NO+35H$_2$O and for oxidizing 1,1-bis-(3,4-dimethylphenyl)-methane (dixylylmethane, DXM) to 3,3',4,4'-benzophenone tetracarboxylic acid (BTA) is

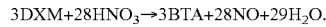
3DXM+28HNO$_3$→3BTA+28NO+29H$_2$O.

Preferably, nitric acid is used in an amount of from 0.9 to 2.0 times the stochiometric amount, preferably from 1.1 to 1.5 times the stochiometric amount. Nitric acid is preferably used as an aqueous solution containing from 30 to 70% by weight nitric acid, more preferably as a concentrated aqueous solution containing from 50 to 70% by weight nitric acid. The reaction is preferably carried out at a nitric acid concentration in the reaction mixture of no more than 30% by weight to prevent nitration of phenyl groups. In a preferred embodiment, the reaction is carried out as a fed batch reaction, charging the 1,1-bis-(3,4-dimethylphenyl)-alkane and water or an aqueous nitric acid solution to the pressure vessel to provide a nitric acid content of no more than 15% by weight in the resulting mixture and feeding an aqueous nitric acid solution comprising from 30 to 70% by weight nitric acid to the pressure vessel over a period of from 1 to 10 h. Preferably, the reaction temperature is increased during the feeding of the nitric acid from an initial value in the range of from 90 to 110° C. to a final value in the range of from 140 to 180° C. A low initial nitric acid concentration in the reaction mixture and a fed batch reaction with a temperature ramp starting at a temperature lower than needed for oxidizing the methyl groups of the dimethylphenyl moiety reduce the formation of byproducts and provides 3,3',4,4'-benzophenone tetracarboxylic acid with better yield and purity.

In the process of the invention, nitric oxide formed from nitric acid during the reaction is passed from the pressure vessel into an absorption vessel and is reacted with molecular oxygen and water in the absorption vessel to produce an aqueous nitric acid solution. The stoichiometry for reacting nitric oxide with oxygen and water in the absorption vessel is

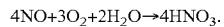
4NO+3O$_2$+2H$_2$O→4HNO$_3$.

Nitric oxide is preferably reacted with oxygen and water in the absorption vessel at a temperature of from 10 to 40° C. and at a pressure of from 1 to 10 bar. The oxygen needed for this reaction is preferably introduced into the absorption vessel by a gas containing at least 98% by volume of oxygen. Any device suitable for contacting gas with a liquid may be used as absorption vessel. Preferably, a stirred tank reactor or an absorption column are used as the absorption vessel. The nitric oxide is preferably passed from the pressure vessel into the absorption vessel via a conduit equipped with a pressure regulating valve set to a pressure which is higher than the vapor pressure at the temperature employed for the reaction in the pressure vessel. The set point for the pressure regulating valve is preferably from 0.1 to 5 bar higher than the vapor pressure at the highest temperature employed for the reaction in the pressure vessel. The pressure setting for this pressure regulating valve may be lowered when the reaction of the 1,1-bis-(3,4-dimethyl-phenyl)-alkane has been completed to purge more nitric oxide from the pressure vessel to the absorption vessel with water vapor evaporating from the reaction mixture in the pressure vessel. Oxygen is preferably introduced into the absorption vessel via a pressure regulating valve set to the operating pressure of the absorption vessel. Preferably, water is charged to the absorption vessel in an amount to provide a nitric acid concentration of from 30 to 70% by weight after all nitric oxide passed from the pressure vessel into the absorption vessel has been reacted. The absorption vessel is preferably flushed with oxygen gas before nitric oxide is passed from the pressure vessel into the absorption vessel. The steps of passing nitric oxide, formed during oxidation of the 1,1-bis-(3,4-dimethylphenyl)-alkane or its partial oxidation product, from the pressure vessel to the absorption vessel and reacting the nitric oxide in the absorption vessel with molecular oxygen and water significantly reduce the amount of nitric oxide discharged from the process and at the same time safely prevent inhibiting the oxidation reaction in the pressure vessel by molecular oxygen.

The nitric acid solution produced in the absorption vessel can be used for the step of oxidizing the 1,1-bis-(3,4-dimethylphenyl)-alkane or a partial oxidation product, which reduces the consumption of nitric acid compared to prior art processes where nitric oxide is discharged from the process. When the oxidation of the 1,1-bis-(3,4-dimethylphenyl)-alkane or its partial oxidation product is carried out as a fed batch reaction, the nitric acid solution produced in the absorption vessel is preferably used in a subsequent batch. When 1,1-bis-(3,4-dimethylphenyl)-methane is used as the 1,1-bis-(3,4-dimethylphenyl)-alkane and oxygen is supplied to the absorption vessel by a gas containing at least 98% by volume of oxygen, the method of the invention can be carried out without discharging gas from the assembly of pressure vessel and absorption vessel during the reaction. In this case, there is no need for cleaning an off gas before discharging it to the atmosphere.

The 3,3',4,4'-benzophenone tetracarboxylic acid, provided by reacting the 1,1-bis-(3,4-dimethylphenyl)-alkane or its partial oxidation product with nitric acid, is preferably separated from the reaction mixture obtained in the pressure vessel, preferably by cooling the reaction mixture to crystallize 3,3',4,4'-benzophenone tetracarboxylic acid and separating the crystallized product from the residual liquid by filtering or centrifuging. The crystallized product may be washed with water to remove by-products.

In a preferred embodiment, the method of the invention is carried out with two subsequent reaction steps. In the first reaction step, the 1,1-bis-(3,4-dimethylphenyl)-alkane is reacted with a first aqueous nitric acid composition at a temperature of from 90 to 115° C. The initial nitric acid content in the reaction mixture is preferably kept in the range of from 10 to 30% by weight to prevent side reactions, such as nitration of the phenyl groups. The first reaction step provides a reaction mixture with two liquid phases, an aqueous phase and an organic phase comprising 3,3',4,4'-tetramethylbenzophenone. The reaction time for the first reaction step is preferably chosen to provide a conversion of the 1,1-bis-(3,4-dimethylphenyl)-alkane of more than 50%, preferably more than 80%. The first reaction step is preferably carried out in a stirred reactor with stirring to disperse the 1,1-bis-(3,4-dimethylphenyl)-alkane in the first aqueous nitric acid composition. The density of the organic phase increases during the first reaction step and the organic phase will reach a higher density than the aqueous phase at sufficient conversion of the 1,1-bis-(3,4-dimethylphenyl)-alkane, making it the heavier phase of the reaction mixture. In a subsequent step, the aqueous phase and the organic phase of the reaction mixture formed in the first reaction step are separated, preferably by settling and withdrawing the organic phase as the bottom phase after settling. Settling may be carried out in the same vessel used for carrying out the first reaction step, in a separate settler vessel or with any other device suitable for separating two liquid phases. Separation of the organic phase from the aqueous phase is preferably carried out at a temperature of more than 50° C., more preferably at a temperature of from 60 to 80° C., to prevent precipitation of solid 3,3',4,4'-tetramethylbenzophenone. The organic phase separated from the reaction mixture of the first reaction step is then reacted with a second aqueous nitric acid composition in a second reaction step carried out in the pressure vessel. The second reaction step is carried out at a temperature of from 120 to 220° C. The second aqueous nitric acid composition is preferably added in an amount which provides a final concentration of nitric acid in the reaction mixture of from 10 to 30% by weight to prevent side reactions. The reaction time for the second reaction step is preferably chosen to provide a conversion of more than 50%, preferably more than 80% of the 3,3',4,4'-tetramethylbenzophenone contained in the organic phase of the reaction mixture formed in the first reaction step. Nitric oxide formed in the second reaction step is passed from the pressure vessel into the absorption vessel and reacted in the absorption vessel with molecular oxygen and water to produce an aqueous nitric acid solution as described further above. Preferably, nitric oxide formed in the first reaction step is also passed to the absorption vessel.

The second reaction step is preferably carried out as a fed batch reaction, feeding an aqueous nitric acid solution comprising from 30 to 70% by weight nitric acid to the pressure vessel over a period of from 1 to 10 h. The reaction temperature is preferably increased during the feeding from an initial value in the range of from 110 to 130° C. to a final value in the range of from 140 to 180° C. Dosing a concentrated nitric acid and increasing reaction temperature during the dosing allows for good temperature control of the exothermal oxidation reaction, which reduces by-product formation, and keeps reaction volume low, which leads to high productivity and improves the yields for recovering 3,3',4,4'-benzophenone tetracarboxylic acid by crystallization.

The reaction mixture of obtained in the second reaction step is preferably cooled to crystallize 3,3',4,4'-benzophenone tetracarboxylic acid, crystallized 3,3',4,4'-benzophenone tetracarboxylic acid is separated from residual liquid, preferably by filtration or centrifugation, and separated residual liquid is passed to the first reaction step to provide at least part of said first aqueous nitric acid composition and preferably all of the first aqueous nitric acid composition.

Reuse of the residual liquid from the second reaction step as oxidant in the first reaction step reduces the amount of nitric acid discharged with effluents from the process and reduces overall consumption of nitric acid.

The 3,3',4,4'-benzophenone tetracarboxylic acid separated from the reaction mixture obtained in the pressure vessel is preferably dehydrated to form 3,3',4,4'-benzophenone tetracarboxylic acid dianhydride. Dehydration can be carried out by any of the processes known from the prior art, such as by heating at reduced pressure or by heating in an inert solvent as described in U.S. Pat. No. 4,684,738.

EXAMPLE

Oxidation of 1,1-bis-(3,4-dimethylphenyl)-methane was carried out in an oil heated jacketed 250 ml glass autoclave equipped with a Hastelloy propeller stirrer and a Hastelloy temperature sensor. The autoclave was connected via a conduit and a pressure regulating valve set to 6.9 bar to a stainless steel absorption vessel equipped with a magnetic stirrer and charged with 40 ml water. The glass autoclave was charged with 28 g of 1,1-bis-(3,4-dimethylphenyl)-methane, 40 g of water and 10 g of 65% by weight nitric acid. 150 g of 65% by weight nitric acid were charged to a feed vessel connected to the glass autoclave via a high-pressure pump. The glass autoclave was closed and heated to 100° C. with stirring before dosing of nitric acid from the feed vessel was started at a feed rate of 0.5 ml/min. The reaction temperature was maintained at 110 to 115° C. for 45 min and was then raised to 145° C. over a 30 min period, increasing the feed rate to 1 ml/h after about 30 min. After all nitric acid from the feed vessel had been added, the temperature was raised to 160° C. and the reaction mixture was stirred for a further 130 min at this temperature before it was cooled to room temperature. During the oxidation, oxygen was supplied to the absorption vessel from a pressure cylinder through a manually operated valve to keep the pressure in the absorption vessel at a pressure of more than 1 bar and less than 6.9 bar. The solid which precipitated after cooling was filtered off, washed with water and dried to provide 35.8 g of 3,3',4,4'-benzophenone tetracarboxylic acid.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

The invention claimed is:

1. A method for oxidizing a 1,1-bis-(3,4-dimethylphenyl)-alkane to 3,3',4,4'-benzophenone tetracarboxylic acid, comprising:
   reacting the 1,1-bis-(3,4-dimethylphenyl)-alkane or a partial oxidation product thereof with nitric acid in a pressure vessel at a temperature of from 120 to 220° C.;
   providing 3,3',4,4'-benzophenone tetracarboxylic acid with formation of nitric oxide;
   passing the nitric oxide from the pressure vessel into an absorption vessel; and
   reacting the nitric oxide in the absorption vessel with molecular oxygen and water to produce an aqueous nitric acid solution.

2. The method of claim 1, wherein the 1,1-bis-(3,4-dimethylphenyl) alkane is bis-(3,4-dimethylphenyl)-methane.

3. The method of claim 1, wherein no molecular oxygen is introduced into said pressure vessel.

4. The method of claim 1, wherein the method comprises using aqueous nitric acid solution produced in the absorption vessel for reacting the 1,1-bis-(3,4-dimethylphenyl)-alkane or a partial oxidation product thereof with nitric acid.

5. The method of claim 1, comprising separating 3,3',4,4'-benzophenone tetracarboxylic acid from the reaction mixture obtained in said pressure vessel.

6. The method of claim 1, wherein the molecular oxygen is introduced into said absorption vessel by a gas containing at least 98% by volume of oxygen.

7. The method of claim 1, wherein the 1,1-bis-(3,4-dimethylphenyl)-alkane is reacted in a fed batch reaction, charging the 1,1-bis-(3,4-dimethylphenyl)-alkane and water or an aqueous nitric acid solution to the pressure vessel to provide a nitric acid content of no more than 15% by weight in the resulting mixture and feeding an aqueous nitric acid solution comprising from 30 to 70% by weight nitric to the pressure vessel over a period of from 1 to 10 h, and increasing the reaction temperature during said feeding from an initial value in the range of from 90 to 110° C. to a final value in the range of from 140 to 180° C.

8. The method of claim 1, comprising the steps:
   a) reacting the 1,1-bis-(3,4-dimethylphenyl)-alkane with a first aqueous nitric acid composition at a temperature of from 90 to 115° C. to provide a reaction mixture with two liquid phases, an aqueous phase and an organic phase comprising 3,3',4,4'-tetramethylbenzophenone;
   b) separating the aqueous phase and the organic phase of step a); and
   c) reacting the organic phase separated in step b) with a second aqueous nitric acid composition in said pressure vessel at a temperature of from 120 to 220° C.

9. The method of claim 8, wherein the reaction mixture of step c) is cooled to crystallize 3,3',4,4'-benzophenone tetracarboxylic acid and residual liquid separated from crystallized 3,3',4,4'-benzophenone tetracarboxylic acid is passed to step a) to provide at least part of said first aqueous nitric acid composition.

10. The method of claim 9, wherein said second aqueous nitric acid composition is added in an amount providing a final concentration of from 10 to 30% by weight nitric acid in the reaction mixture resulting from step c).

11. The method of claim 8, wherein nitric oxide formed in step a) is passed to said absorption vessel.

12. The method of claim 8, wherein step c) is carried out as a fed batch reaction, feeding an aqueous nitric acid solution comprising from 30 to 70% by weight nitric acid to the pressure vessel over a period of from 1 to 10 h, increasing the reaction temperature during said feeding from an initial value in the range of from 110 to 130° C. to a final value in the range of from 140 to 180° C.

13. The method of claim 1, wherein 3,3',4,4'-benzophenone tetracarboxylic acid is separated from the reaction mixture obtained in the pressure vessel and is dehydrated to form 3,3',4,4'-benzophenone tetracarboxylic acid dianhydride.

14. A method for oxidizing a 1,1-bis-(3,4-dimethylphenyl)-alkane to 3,3',4,4'-benzophenone tetracarboxylic acid, comprising the steps:
   a) reacting the 1,1-bis-(3,4-dimethylphenyl)-alkane with a first aqueous nitric acid composition at a temperature of from 90 to 115° C. to provide a reaction mixture with two liquid phases, an aqueous phase and an organic phase comprising 3,3',4,4'-tetramethylbenzophenone;
   b) separating the aqueous phase and the organic phase of step a);
   c) reacting the organic phase separated in step b) with a second aqueous nitric acid composition a pressure vessel in a fed batch reaction, feeding an aqueous nitric acid solution comprising from 30 to 70% by weight nitric acid to the pressure vessel over a period of from 1 to 10 h, increasing the reaction temperature during said feeding from an initial value in the range of from 110 to 130° C. to a final value in the range of from 140 to 180° C.;
   d) passing nitric oxide from the pressure vessel into an absorption vessel; and
   e) reacting the nitric oxide in the absorption vessel with molecular oxygen and water to produce an aqueous nitric acid solution.

15. The method of claim 14, wherein all or a part of the aqueous nitric acid solution produced in step e) is passed to step c) for supplying said second aqueous nitric acid composition.

16. The method of claim 14, wherein the reaction mixture of step c) is cooled to crystallize 3,3',4,4'-benzophenone tetracarboxylic acid and residual liquid separated from crystallized 3,3',4,4'-benzophenone tetracarboxylic acid is passed to step a) to provide at least part of said first aqueous nitric acid composition.

17. The method of claim 16, wherein the crystallized 3,3',4,4'-benzophenone tetracarboxylic acid is separated from the reaction mixture and is dehydrated to form 3,3',4,4'-benzophenone tetracarboxylic acid dianhydride.

18. A method for oxidizing a 1,1-bis-(3,4-dimethylphenyl)-alkane to 3,3',4,4'-benzophenone tetracarboxylic acid, comprising the steps
   a) reacting the 1,1-bis-(3,4-dimethylphenyl)-alkane in a fed batch reaction, charging the 1,1-bis-(3,4-dimethylphenyl)-alkane and water or an aqueous nitric acid solution to a pressure vessel to provide a nitric acid content of no more than 15% by weight in the resulting mixture and feeding an aqueous nitric acid solution comprising from 30 to 70% by weight nitric to the pressure vessel over a period of from 1 to 10 h, increasing the reaction temperature during said feeding from an initial value in the range of from 90 to 110° C. to a final value in the range of from 140 to 180° C.;

b) passing nitric oxide from the pressure vessel into an absorption vessel;

c) reacting the nitric oxide in the absorption vessel with molecular oxygen and water to produce an aqueous nitric acid solution; and d) passing all or a part of the aqueous nitric acid solution produced in step c) to a subsequent batch of step a).

19. The method of claim 18, wherein the reaction mixture of step a) is cooled to crystallize 3,3',4,4'-benzophenone tetracarboxylic acid and residual liquid separated from crystallized 3,3',4,4'-benzophenone tetracarboxylic acid is recycled to a subsequent batch of step a).

20. The method of claim 18, wherein the reaction mixture of step a) is cooled to crystallize 3,3',4,4'-benzophenone tetracarboxylic acid, the crystallized 3,3',4,4'-benzophenone tetracarboxylic acid is separated from the reaction mixture and is dehydrated to form 3,3',4,4'-benzophenone tetracarboxylic acid dianhydride.

* * * * *